United States Patent [19]

Amer

[11] Patent Number: 5,780,487
[45] Date of Patent: Jul. 14, 1998

[54] S-2'-[2-(1-METHYL-2-PIPERIDYL) ETHYL] CINNAMANILIDE

[76] Inventor: Moh. Samir Amer, 877 Sandpoint Rd., Carpinteria, Calif. 93013

[21] Appl. No.: 810,503

[22] Filed: Feb. 28, 1997

Related U.S. Application Data

[63] Continuation-in-part of Ser. No. 512,235, Aug. 7, 1995, Pat. No. 5,605,902.
[51] Int. Cl.[6] ............ A61K 31/445; C07D 211/32
[52] U.S. Cl. ............................ 514/331; 546/234
[58] Field of Search ................... 514/331; 546/234

[56] References Cited

U.S. PATENT DOCUMENTS

| | | | |
|---|---|---|---|
| 4,000,143 | 12/1976 | Dykstra et al. | 260/293.67 |
| 5,266,571 | 11/1993 | Amer | 514/252 |
| 5,605,902 | 2/1997 | Amer | 514/252 |

*Primary Examiner*—Raymond Henley, III
*Attorney, Agent, or Firm*—Samson B. Leavitt; Michael A. Leavitt

[57] ABSTRACT

The 5HT$_2$ receptor antagonizing effect of 2'-[2-(1-methyl-2-piperidyl) ethyl] cinnamanilide, a racemic mixture (R S-MPEC) of S-MPEC and R-MPEC isomers is found to be provided practically entirely by the S-MPEC isomer, the R-MPEC being effectively an impurity. Disclosed are pure S-MPEC, mixtures thereof with up to about 10% of R-MPEC, a novel method of resolving the S-MPEC involving a novel intermediate compound, therapeutic compositions containing S-MPEC, and uses thereof for administration to animals, especially humans, in need of 5HT$_2$ receptor blockage, as for hemorrhoids, varicose veins, venous and coronary insufficiencies, wound healing, and as analgesic or local anesthetic agents.

19 Claims, No Drawings

S-2'-[2-(1-METHYL-2-PIPERIDYL) ETHYL] CINNAMANILIDE

This application is a continuation-in-part of application Ser. No. 08/512,235 filed Aug. 7, 1995, now U.S. Pat. No. 5,605,902.

FIELD OF THE INVENTION

This invention relates to a specific isomer, namely a specific S (or(−)or l or levo) isomer, in particular die compound S-2'- [2-(1-methyl-2-piperidyl) ethyl] cinnamanilide or its acid salt, its preparation and its use in therapeutic treatments and compositions as a 5-$HT_2$ receptor antagonist (blocker) for treating or preventing hemorrhoids, varicose veins, or venous or coronary insufficiency, treating wounds or as analgesic or local anesthetic agents in animals including mammals, especially humans.

BACKGROUND OF THE INVENTION

In my U.S. Pat. No. 5,266,571 dated Nov. 30, 1993, the entire disclosure of which is incorporated herein by reference thereto, I have disclosed and claimed a method for treating or preventing hemorrhoids in animals by administration of a 5-$HT_2$ receptor antagonist based on the discovery that 5-HT (5-hydroxytryptamine or serotonin) plays an important role in mediating both the increase in venous pressure and/or platelet clumping that lead to the congestion of the veins in the hemorrhoidal plexus, that 5-$HT_2$ receptors rather than 5-$HT_1$ receptors are involved, and that 5-$HT_2$ receptor antagonists thus inhibit hemorrhoids. As such preferred antagonists are mentioned 2'- [2-(1-methyl-2-piperidyl) ethyl] cinnamanilide hydrochloride (MPEC) and two other compounds.

In my U.S. patent application Ser. No. 08/512,235 filed Aug. 7, 1995, now U.S. Pat. No. 5,605,902, the entire disclosure of which is herein incorporated by reference thereto, which prior U.S. application corresponds to PCT WO94/18958 published Sep. 1, 1994, I further disclose and claim the use of the same 5-$HT_2$ receptor antagonists for treating or preventing varicose veins or venous insufficiency or for treating wounds.

OBJECTS OF THE INVENTION

It is an object of this invention to provide a new and improved form or species of 5-$HT_2$ receptor antagonist, a new intermediate compound for making such antagonist, methods and means for preparing such intermediate and antagonist, and use of such antagonist in therapeutic treatments and compositions.

Another object of this invention is to provide a new, improved, purer, unadulterated and/or more effective form of MPEC for use in such treatments and compositions.

Other objects and advantages will appear as the description proceeds.

SUMMARY OF THE INVENTION

In accordance with certain of its aspects, the attainment of one or more of the foregoing objects is made possible by this invention which comprises separating the racemic (RS) MPEC mixture employed in the inventions of my said two prior U.S. applications into its individual S and R(or(+)or d) isomers and discovering that the R isomer is totally or substantially devoid of any activity as a 5-$HT_2$ receptor antagonist and is in that respect an adulterant or impurity in any mixture with the S isomer, in which mixture the S isomer is the only active 5-$HT_2$ receptor antagonist, and that the S isomer (S-MPEC) is thus unexpectedly at least twice as effective as a 5-$HT_2$ receptor antagonist as the racemic MPEC mixture (RS-MPEC). Thus, the 5-$HT_2$ receptor blocking effect achieved with any given amount of the RS-MPEC can be achieved with say half that amount of the S-MPEC. Other disadvantages would be inherent in any therapeutic composition containing an equal amount of active ingredient and adulterant. The isomeric and racemic forms of MPEC have in common the empirical formula $C_{23}H_{28}N_2O$. (M.W.348.49).

DETAILED DESCRIPTION OF THE INVENTION

This invention comprises the provision, use in therapeutic compositions and in treatment of animals in need of a 5-$HT_2$ receptor blocking effect, of compounds or mixtures thereof selected from the group consisting of R isomer-free S-2'-[2-(1-methyl-2-piperidyl) ethyl] cinnamanilide (S-MPEC), a pharmaceutically acceptable acid salt thereof, and any mixtures thereof with up to about 10% of any of their corresponding R-isomers (R-MPEC) and salts thereof.

The aforesaid mixtures preferably contain no more than about 4%, more preferably no more than about 1%, of the R-MPEC impurity, the S-MPEC is preferably the hydrochloride salt, and/or the S-MPEC is preferably devoid of R-MPEC. The term "substantially free of the R isomer" (or equivalent) is intended to cover mixtures containing from about 0.0001% to about 10% of the R isomer (stereoisomer).

The invention also comprises the production of a novel intermediate, S-[2-(o-aminophenethyl)-1-methyl piperidine-dibenzoyl-L-tartrate salt] (S-APEMP.DBLT (or.L-DBT)) comprising reacting 1 mol of 2-nitrobenzaldchyde with 1 mol of 2-picoline in the presence of acetic anhydride and treating the resulting 2-(o-nitrostyryl)-pyridine with a quartermizing methylating agent to produce the corresponding 2-(o-nitrostyryl)-1-methylpyridinium (NSMP) salt, reducing the pyridinium salt by catalytic hydrogenation to produce the corresponding RS-2- (o-aminophenethyl)-1-methylpiperidine (RS-APEMP) hydro salt, treating the hydro salt with an alkaline agent to liberate the free base (RS-APEMP) and treating the free base with dibenzoyl-L-tartaric acid (DBLT or L-DBT) to produce the novel S-APEMP-DBLT. The latter is then treated with an alkaline agent to liberate the free base (S-APEMP) which is then reacted with an equimolar amount of cinnamoyl chloride to produce S-MPEC.

In the above process, the initial steps for producing the NSMP salt are disclosed in Dykstra et al. J. Med. Chem 16 1015 (1973) and L. Horwitz. J. Org. Chem. 21 1039 (1956), and the next step of producing APEMP hydro salt is disclosed in Dykstra. et al. U.S. Pat. No. 4,064,254, especially EXAMPLE 1. EXAMPLES 1, 25 and 141 of the latter patent disclose the production of the "l"-MPEC and "d"-MPEC separately using procedures quite similar to applicant's above-described process except that the separation is achieved with d-camphoric acid in 95% ethanol (instead of applicant's dibenzoyl-L-tartaric acid) and requires fractional crystallization which is inefficient. Also, the −42.8° optical rotation reported in the patent for the "l"-MPEC indicates a reduced efficiency (compared with applicant's S-MPEC product with a −46° optical rotation).

It is further significant that this '254 patent discloses no recognition of any possibility that the properties of the S and R isomers of MPEC might differ, much less that one isomer might be completely inactive in a field in which the other isomer is highly active, much less when that activity is for blocking 5-$HT_2$ receptors, much less for treating or preventing hemorrhoids, varicose veins or venous or coronary insufficiency or treating wounds or as analgesic or local anesthetic agents. Applicant's U.S. Pat. No. 5,266,571 discussed the insufficiency of prior art suggesting antiserotonin activity broadly as a basis for urging anticipation of an invention based on 5-$HT_2$ receptor antagonism. A similar situation exists here, the only activity disclosed in the '254 patent being antiarrythmia and antiserotonin.

The S-MPEC (or its salt) in pure form or containing the slight indicated amounts of the inactive R isomer impurity, may be provided and used in free form or in or with a non-toxic pharmaceutically acceptable solid, liquid or particulate carrier in the form of a paste, ointment, cream or gel composition suitable for topical or rectal administration, desirably with a gelling, binding or thickening agent to provide the desired viscosity, or in the form of a tablet, capsule, chewing gum, lozenge, powder, spray, aerosol, enema, suppository, syrup, elixir, aqueous or oily suspension, emulsion or solution, paste, ointment, cream or gel suitable for systemic oral, rectal or parenteral administration as by subcutaneous, intraperitoneal, intramuscular or intravenous injection or by transdermal or inhalation therapy.

The S-MPEC may be employed in free form or as a generally water soluble non-toxic pharmaceutically acceptable acid addition salt with such relatively non-toxic organic or inorganic acids as sulfuric, sulfonic, phosphoric, phosphonic, hydrobromic, hydrochloric, hydroriodic, sulfamic, methanesulfonic, benzenesulfonic, para-toluenesulfonic, acetic, lactic, succinic, malic, mucic, tartaric, citric, gluconic, benzoic, cinnamic, isethionic and the like.

Suitably the compositions of this invention comprise sufficient active S-MPEC material to provide a dose of from 0.05–10 mg. per kg. of body weight, more suitably 0.2–6 mg/kg body weight. These compositions may be taken 1–3 times daily or as needed until the symptom or condition being treated subsides or is corrected.

The compositions of this invention may contain the active ingredient in amounts ranging from less than 1% to over 99%, with any remainder being a pharmaceutically acceptable solid or liquid carrier, which may contain other conventional excipients. Examples of such carriers and excipients include fillers, binders, flavors, sweeteners, bulking and coloring agents, antioxidants, anionic, nonionic, cationic, zwitterionic, and amphoteric surface active detergents, sudsing, dispersing and emulsifying agents, buffering and pH adjusting agents, water and organic solvents, humectants, thickeners, preservatives, stabilizers, mold release agents, disintegrants, anti-disintegrants, lubricants and the like. Examples of conventional pharmaceutically acceptable carriers and excipients are profusely disclosed in the prior art including discussions in U.S. Pat. No. 4,515,772 (Parran et al, Proctor & Gamble), U.S. Pat. No. 4,966,777 (Gaffar et al, Colgate-Palmolive Company), and U.S. Pat. No. 4,728,512 (Mehta et al, American Home Products), which discussions are incorporated herein by reference thereto.

The following examples are only illustrative of certain preferred embodiments of this invention. All parts and proportions referred to herein and in the appended claims are by weight and temperatures are in degrees Centigrade, unless otherwise indicated.

Example 1 below illustrates by equation and description one preferred embodiment of a method of making S-MPEC, with supporting data characterizing, identifying and/or corroborating the properties of intermediates, final products, etc.

EXAMPLE 1

Preparation and Confirmation of S-MPEC

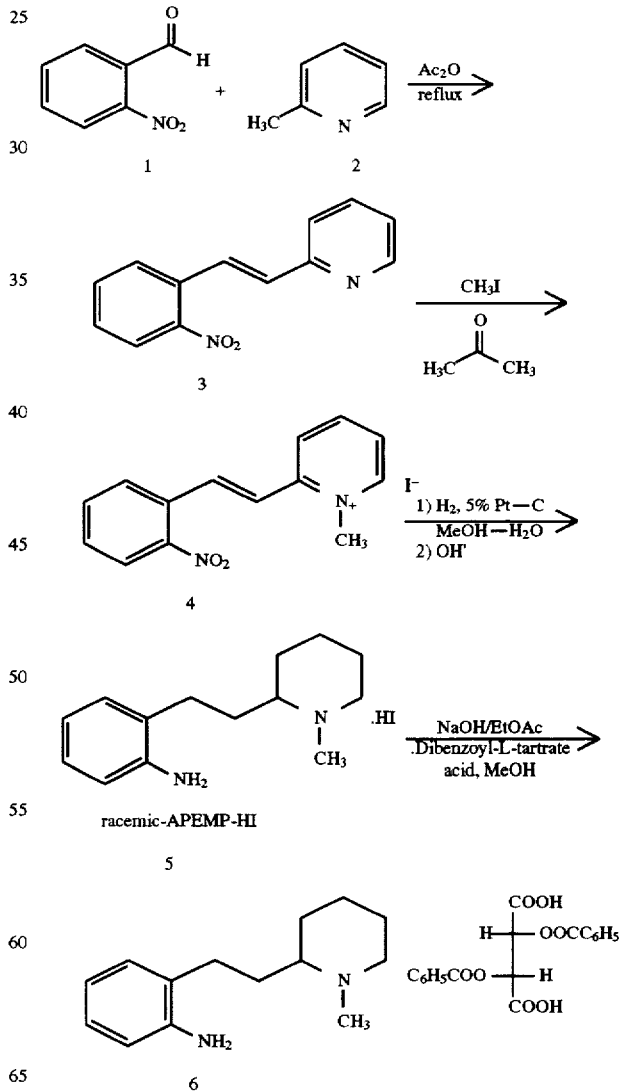

FIGURE 1

-continued
FIGURE 1

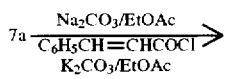

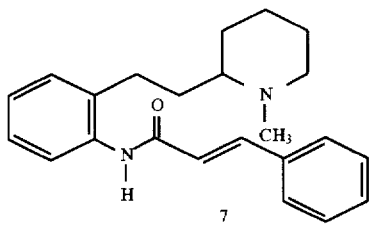

1. 2-nitrobenzaldehyde
2. 2-picoline
3. 2-(o-nitrostyryl)pyridine (NSP)
4. 2-(o-nitrostyryl)-1-methylpyridinium iodide
5. RS-2-(o-aminophenethyl)-1-methylpiperidine. HI
6. S-[2-(o-aminophenethyl)-1-methylpiperidine-dibenzoyl-L-tartrate] (S-APEMP. DBLT or L-DBT)
7. S-2'-|2-(1-methyl-2-piperidyl)ethyl|cinnamanilide (S-MPEC)
7a. Cinnamoyl chloride S-MPEC Chemical Process (A) 2-(o-Nitrostyryl) -1-Methylpyridinium Iodide (NSMP-I)

To a 50 L round bottomed flask was added 2-nitrobenzaldehyde (3.500 g. 23.2 moles). 2-picoline (3.2 L., 32.8 moles) and acetic anhydride. The mixture was stirred efficiently under an inert atmosphere (nitrogen or another inert gas) and heated to reflux for 27 hrs. The mixture was cooled to under 100 C., for safe handling, and quenched in a suitable vessel equipped with external cooling and efficient stirring on 10.5 Kg. of ice. The pH was adjusted to 11 with 45% aqueous sodium hydroxide at a rate to keep the temperature below 50° C. After cooling to 20°–30° C. the granular solid was collected by filtration, washed well with water. Yield 6572 g. of crude 2-(o-nitrostyryl) pyridine (NSP).

This solid was transferred to a 50 L. round bottomed flask, dissolved in acetone (14 L.) and iodomethane (2.94 L., 47.7 moles) (quaternizing methylating agent) was added. (Other such (alkylating) agents may be used, generally having the formula $CH_3X$. X being an anion such as sulfate, methyl sulfate, halide (Cl, Br, I), etc.). The mixture was heated to reflux under an inert atmosphere (nitrogen or another inert gas) for 18 hrs. After cooling to 20° C. the precipitate was collected by filtration and washed with acetone or a 1:1 mixture of acetone: ethyl acetate (3×3.5 L.). Drying to constant weight at 50°–60° C. yielded 6.839 g. (80%) of NSMP.I.

(B) RS-2-(o-Aminophenethyl)-1-Methylpiperidine, Hydroiodide (RS-APEMP.HI)

In a 5 gallon reactor, a solution of NSNP.I (935 g., 2.5 moles) in methanol (14 L.) was reduced in a hydrogen atmosphere (Psi. 55) in the presence of Pt/C (5 or 10%, 98 g.). After removal of the catalyst and evaporation of the filtrate in the usual manner, the residue was dissolved in hot methanol (2.8 L.). Ethyl acetate (2.8 L) was added to the hot mixture to induce crystallization, yield 516.3 g. (59%) of RS-APEMP.HI.

(C) S-[2-(o-Aminophenethyl)-1-Methylpiperidine Dibenzoyl-L-Tartrate] (S-APEMP.DBLT)

A solution of RS-APEMP.HI (516 g., 1.5 mole) ethyl acetate (5.5 g.) (or other low boiling water immiscible solvent such as benzene, toluene etc.) was extracted with 5% aqueous sodium hydroxide to liberate the free base (organic phase), washing the organic phase with water, drying over a suitable drying agent (such as anhydr. sodium sulfate, magnesium sulfate, potassium carbonate etc.) After separating the solvent from the drying agent the solution was evaporated in vacuo and the residual RS-APEMP free base was dissolved in methanol (1.0. L.) and a solution of dibenzoyl-L-tartaric acid (540 g., 1.5 moles) in methanol (2.3 L.) was added. The mixture was held overnight at room temperature. The crystalline precipitate was collected and recrystallized from methanol (3.4 L.), yield 246 g. of S-APEMP.DBNLT. (28.6%, wt; 57.2% of the S-APEMP).

(D) S-2'-|2-(1-Methyl-2-Piperidyl)ethyl| Cinnamanilide (S-MPEC)

A solution of S-APEMP.DBLT (287 g, 0.5 mole) in ethyl acetate (3.2 L.) (or other low boiling water immiscible solvent) was extracted with 7.5% aqueous sodium bicarbonate (3.2 L.) to liberate the S-APEMP. After a water wash and drying over a suitable drying agent the solvent was removed in vacuo. The oily residue, S-APEMP, was dissolved in ethyl acetate (1.0 L.) and anhydrous potassium carbonate (412 g, 3.0 moles) (or other suitable acid acceptor such as triethyl amine, pyridine etc.) was added. Cinnamoyl chloride (143 g., 0.7 mole) in 700 ml. of ethyl acetate was added slowly. After the initial reaction, the mixture was refluxed for 14 hrs. After cooling to room temperature the mixture was extracted with water (1.7 L.) and dried over a suitable drying agent. After removing the drying agent the solvent was removed in vacuo and the residue was dissolved in hot ethyl acetate (280 ml.) and allowed to slowly cool to room temperature; filtration yielded S-MPEC. (136 g., 79% yield). Analysis: Calcd. For C, H, N: C, 79.27; H, 8.10; N, 8.04. Found: C, 79.27; H, 8.06; N, 8.07. HPLC(chiral)purity: 99.5%, $|\alpha|_{D25°}=-46°$ (c=0.01.EtOH); Melting point: 128° C.

Absolute Configuration of I-MPEC

Summary

Absolute configuration of 1-MPEC was determined to be S by X-ray crystallography of 1-APEMP.L-DBT.2H$_2$O, which is an intermediate of 1-MPEC.

Since elaboration to grow crystals of 1-MPEC did not yield any successful results, recrystallization of fine crystals of 1-APEMP.L-DBT, which is an intermediate of 1-MPEC, was then tried. Slow recrystallization of 1-APEMP.L-DBT gave large enough crystals of corresponding dihydrate.

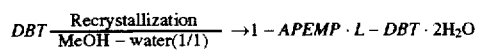

Absolute configuration of 1-APEMP.L-DBT.2H$_2$O was determined to be S by X-ray crystallography. Configuration of 1-APEMP.L-DBT is retained under reaction conditions of which conversion to 1-MPEC shown in FIG. 1, because cinnamoyl chloride reacts only with amino group on the benzene ring, and does not affect any other part of the molecule. Consequently, absolute configuration of 1-MPEC was determined to be S.

Experimental 500 mg of fine crystals of 1-APEMP.L-DBT, of which stereochemical purity was>99.5% d.e., was dissolved in 10 mL of methanol/water (1/1) and the crystals were grown up for 7 days at room temperature, to give crystals of 1-APEMP.L-DBT.2H$_2$O. Experimental details and results of the X-ray crystallography are summarized in Table 1.

The equipments used for the X-ray crystal structure analysis of the 1-APEMP-L-DBT salt were as follows:

Measuring device: ENRAF NONIUS CAD4 (an automatic X-ray diffractometer for single crystal)
Measuring software: Express®
Computer for analysis: DEC VAX3100
Software for analysis: Molen®

TABLE I

X-ray crystallography of l-APEMP-L-DBT.2H$_2$O

| | |
|---|---|
| Sample Name: | I-APEMP.L-DBT.2H$_2$O |
| Molecular Formulas: | C$_{32}$H$_{36}$N$_2$O$_8$.2H$_2$O |
| X-rays: | CuKα (λ = 1.54184 Å) |
| Crystal Size (mm): | 0.4 × 0.3 × 0.3 |
| Crystal System: | Orthorhombic |
| Space Group: | P2$_1$ 2$_1$ 2$_1$ |
| a (Å): | 13.3583 (7) |
| b (Å): | 30.298 (2) |
| c (Å): | 7.8105 (6) |
| vol. (Å): | 3161.2 (5) |
| z: | 4— |
| 2 θ (deg.): | 6.4 < 2θ <150 |
| D (calcd.): | 1.287 |
| R*: | 0.052 |
| Number of Reflections: | 3724 |
| Number of Parameter used: | 518 |
| μ (CuKα) (cm$^{-1}$): | 1.89 |
| Number of I > 3 σ (I): | 3476 |
| Maximum e/Å$^3$: | 0.239 |
| Standard Reflection: | 24 points (8 < θ 14) |
| Data Correction Method: | Lorentz and Polarization Effect |
| Reflection Data Collection: | Enraf Nonius CAD-4 System |
| Structure Determination: | Enraf Nonius MolEN Program |

*R = (Σ I I F0 I − I Fe I I)/Σ I F0 I

TABLE 2

CERTIFICATE OF ANALYSIS
Compound Name (−)-2'-[2-(1-Methyl-2-piperidyl)ethyl]cinnamamilide(l-MPEC, S-MPEC)

| TEST | SPECIFICATION | RESULTS |
|---|---|---|
| Physical Description | White to off-white solid with no visible contaminants | White to off-white solid with no visible contaminants |
| $^1$H NMR (CDCl$_3$) 300 MHz | Conforms to Spectrum #B3-13055 | Spectrum #B3-16514 conforms to Spectrum # B3-13055 |
| FTIR (Neat, Acetone) | Conforms to Spectrum #FT0155 | Spectrum #FT0712 conforms to Spectrum # FT0155 |
| R.O.I. | ≦0.1% | 0% |
| Melting Point | Record | 128° C. |
| HPLC (Chemical) | Chemical Purity ≧98% with no single impurity over 0.5% | same |
| HPLC (Chiral) | Chiral Purity ≧99.5% | >99.5% |
| GC (Residual solvents) | Acetone ≦0.2% | <0.1% |
| | Ethyl Acetate = 0.2% | −0.13% |
| | Methanol ≦0.2 | <0.1% |
| | Hexane ≦0.2% | <0.1% |
| Water Content (Karl Fisher) | ≦5.0% | 0.2% |
| Heavy Metals | ≦0.005% | <0.005% |
| Optical Rotation (EtOH) | Record | −46° |
| Elemental Analysis | C 79.27 ± 0.4 | 79.27 |
| | H 8.10 ± 0.4 | 8.06 |
| | N 8.04 ± 0.4 | 8.07 |

TABLE 3

CERTIFICATE OF ANALYSIS
Compound Name: d-2'-[2-(1-Methyl-2-piperidyl)ethyl]cinnamamilide (R-MPEC, (30 )-MPEC)

| TEST | RESULTS |
|---|---|
| Physical Description | White solid, with no visible contaminants |
| $^1$H NMR (CDCl$_3$) 300 MHz | Spectrum #B3-16942 conforms to structure |
| FTIR (Neat, Acetone) | Spectrum #FT0798 conforms to structure |
| MP | 128° C. |
| Elemental Analysis | C - 79.19% |
| | H - 8.09% |
| | N - 8.03% |
| HPLC (Chemical) | 99.8% with no single impurity >0.5% |
| HPLC (Chiral) | 99.9% |
| R.O.I. | <0.1% |
| GC (Residual solvents) | Acetone <0.2% |
| | Ethyl Acetate −0.3% |
| | Methanol <0.2% |
| | Hexane <0.2% |
| | Ethanol <0.2% |
| Water Content (Karl Fischer) | 0.4% |
| Heavy Metals | <0.005% |
| Additional Testing: Optical Rotation (c = 0.01, EtOH | +41° |

EXAMPLE 2
Effects of MPEC in Isolated Human Colon Vein Contracted with 5-hydroxytryptamine (5-HT)

The aim of this study was to determine the IC$_{50}$ of MPEC in isolated human colon vein contracted by 5-hydroxytryptamine. MPEC was tested under three forms: the racemate, the R-isomer and the S-isomer in order to identify the active isomer. Stock solutions of MPEC (10$^-$2M) (racemate, R and S-isomers) were prepared in acidified water (water—hydrochloric acid, 99.50–0.50%) and subsequently diluted in water.

5-HT (5-hydroxytryptamine or serotonin) was dissolved in water at $10^{-2}$M and subsequently diluted in water.

Water used in this study was obtained from a Milli Q apparatus (Millipore).

Human colon veins were obtained from patients (4 males and 2 females, 60±7 years old) undergoing resection of a part of the colon because of colon malignancy or polyposis. Immediately after surgical removal, a colon vein specimen was taken and immediately transported to the laboratory in physiological aqueous saline solution of the following composition (in mM): NaCl (112), KCl (5), NaHCO$_3$ (25) glucose (11.5), KH$_2$PO$_4$ (1.2), CaCl$_2$ (2.5) and MgSO$_4$ (1.2), pH 7.4. This solution was maintained at 37° C. (portable thermostated box, Veba Meditemp) and gassed with oxygen. Under stereo microscope, rings of the human colon veins (3–5 mm, 9.6±1.1 mg, n=25) without fat were prepared and mounted, under 500 mg. of resting tension, in a 25 mL organ bath containing physiological saline solution maintained at 37° C. (low-temperature thermostat Lauda RCS6) and gassed with 95% $O_2$ and 5% $CO_2$. Tension was measured isometrically with a transducer (Grass FT 03) connected to an amplifier (bridge coupler type 570, Hugo Sach Electronic) coupled to an oscillographic recorder (Graphtec linearecorder mark VII WR 3101, Hugo Sach Elektronik) and a computer for data acquisition and control of electro-valves (Amstrad PC 1512SD equipped with AD/DA card and IO card).

Each ring was allowed to equilibrate for 60 min. in physiological saline solution. After this period, the human colon vein was stimulated by 5-HT (3. $10^{-6}$M, concentration inducing a sub-maximal phasic contraction). When the maximal tension was observed, the colon vein was washed with physiological saline solution every 10 min. for 40 min. Once reproducible control contractions had been obtained, the preparations were incubated for 60 min. with MPEC (the racemate form, the S- or the R-isomer) at one fixed concentration: $10^{-9}$, $3.10^{-9}$ or $10^{-8}$M or with water as control before a last contraction induction by 5-HT $3.10^{-6}$M. Only preparations in which the control contractions were matched were used. Preparations developing a tension lower than 250 mg. or weighing less than 2 mg. were discarded. No statistical difference of the control parameters values was observed between the different experimental groups.

The observed inhibition induced by MPEC was expressed as percentage of the last control contraction. The pD'$_2$ (the negative logarithm of the molar concentration of an antagonist capable of reducing to 50% the maximal response caused by an agonist) was calculated by the method of Van Rossum (1963). Only data relating to concentration of inhibitor which produced a mean inhibition between 10 and 90% were used. IC$_{50}$ was calculated as the antilogarithm of pD'$_2$.

Results were expressed as means±standard error of mean. Comparison between two means was made using the Student t test after checking variance homogeneity by $X^2$ test. Comparison among different means was made using an F test (variance analysis with one classification parameter) after checking homogeneity of the variances using Bartlett's test (Lambert, 1963).

TABLE 4

|  | RS-MPEC | S-MPEC | R-MPEC | Selectivity* | Signification |
|---|---|---|---|---|---|
| pD'$_2$ | 8.35 | 8.77 | 7.23 | 34.67 | P < 0.001 |

*selectivity calculated as the antilog of the difference between the two pD'$_2$ values ((Furchgott, 1972). So, MPEC present a stereoselective activity.

The above results indicate that S-MPEC is 34.67 times as active as R-MPEC (thrice as active as RS-MPEC) in blocking 5-HT$_2$ receptors in human colon veins. This is the principal mechanism of the activity of MPEC against hemorrhoids, varicose veins, venous and coronary insufficiency, wound healing and other 5HT$_2$ receptor-induced symptoms. R-MPEC is here shown to be essentially inactive and effectively an impurity.

EXAMPLE 3

Effects of MPEC on Phenylquinone-Induced Writhing in Mice

Mice dosed orally with certain analgesics, tranquilizers or anxiolytics do not respond in a typical manner to an intraperitoneal dose (2.5 mg/kg) of phenyl-p-benzoquinone (PPB). The usual response is writhing, characterized by stretching and twisting of the body. Blockade of this response is measured by comparing the number of writhing episodes observed at different dose levels of the test compound with those observed in vehicle control animals. The writhing episodes for five animals are counted simultaneously with a 5-key laboratory counter. The total number of writhing episodes are counted for each mouse for exactly 10 min. after PPB injection.

Results of testing RS-, R-, and S- MPEC in the above procedure with a saline control and a known analgesic Indomethacin are shown in the following table:

TABLE 5

|  | Dose (mg/kg) | N | No. of Writhing |
|---|---|---|---|
| Saline |  | 10 | 21.4 ± 4.6 |
| Indomethacin | 5 | 9 | 12.8 ± 3.5 |
| RS-MPEC | 2.5 | 9 | 15.3 ± 4.1 |
| R-MPEC | 2.5 | 9 | 25.3 ± 4.2 |
| S-MPEC | 2.5 | 9 | 11.4 ± 3.2 |

The above results show that R-MPEC permitting 25.3 writhings is substantially inactive as an analgesic, and S-MPEC permitting only 11.4 writhings provides substantially all the analgesic activity of the mixture of S-MPEC and R-MPEC in RS MPEC permitting 15.3 writhings. The surprisingly high analgesic activity of S-MPEC is an important property in the treatment of hemorrhoids, wounds and varicose veins and also useful often in treating venous and coronary insufficiencies.

EXAMPLE 4

Blockage of 5-HT$_2$ Receptors on Rat Forebrain

Rats were sacrificed by decapitation to remove the cerebral cortex, to which a 10-fold volume of 0.32M sucrose solution was added for homogenization with POLYTRON (setting: 6 and 30 seconds, KINEMATICA AG, Switzerland). Subsequently 10-minute centrifugation was conducted at 1,000×G. The resulting supernatant was subjected to 20-minute centrifugation at 35,000×G, and a 10-fold volume of 50 nM Tris buffer (pH: 7.4; 25° C.) was added to the precipitate obtained before conducting resuspension. This suspension was subjected to 10-minute incubation at 37° C. before conducting 20-minute recentrifugation at 35,000×G. The final precipitate was suspended in a 40-fold volume of buffer for measurement (50 mM Tris, 4 mM $CaCl_2$, 10 µM pargyline, 0.1% ascorbic acid, pH: 7.7, 25° C.), and this suspension was used as the membrane preparation in the binding experiment. $^3$H-Ketanserine 0.1 ml. (Final concentration:0.4 nM) and 0.4 ml. of the membrane preparation were added to the test drug (S-MPEC and R-MPEC) and to 0.5 ml. of buffer for measurement in which final concentration (1 µM) of methysergide was dissolved. The solution was prepared to make the total volume of 1.0 ml. and was allowed to react at 37° C. for 20 minutes. Following the completion of the reaction, the reactive solution was filtered by aspiration under reduced pressure using the 0.1% polyethyleneimine solution-impregnated Whatmann GF/C filter, and the filter was washed three times with 5 ml. of 50 mM Tris buffer (pH: 7.4, 25° C.) which was immediately cooled with ice, to which 5 ml. of scintisol was added to measure the radioactivity on the filter with a liquid scintillation counter. The specific binding volume was determined to be the value obtained after deduction of the nonspecific binding volume under the presence of 1 µM methysergide from the total binding volume. All the experiment was conducted on a triplication basis. Protein assay of the membrane preparation used was conducted according to the method of Lowry et al.

Results of testing S-MPEC and R-MPEC in the above procedure are shown in the following table:

TABLE 6

|  | S-MPEC | R-MPEC |
|---|---|---|
| $IC_{50}(MM)$ | 1.73 | 116 |

The above results show that S-MPEC is 67 times (116/1.73) as potent as R-MPEC in blocking 5-$HT_2$ receptors from rat forebrains.

EXAMPLE 5

Effect of MPEC on Serotonin Plus Collagen-induced Pulmonary Thromboembolic Death in Mice Purpose Serotonin plays an important role in thrombus formation. The antiserotonergic activity of MPEC is investigated through an inhibition of thromboembolic death.

Animals

Male ddY strain mice

Reference Drug

Ticlopidine, clinically used as an antithrombotic.

Test Drugs

S-MPEC, R-MPEC

Method

Mice are used after overnight fasting. Acute pulmonary thromboembolism is induced by a rapid injection of the mixture serotonin (50 ug/10 g b.w.) and collagen (10 u g/10 g b.w.) into the tail vein and then the mortality of mice within 10 min. is determined. Drugs are administered intra-rectally 1 hr. or orally 3 hr. prior to injection of serotonin and collagen. For oral administration the drug is suspended in Tween 80/distilled $H_2O$ (0.5% vol./vol.), and for intra-rectal dispersed in white petrolatum.

In this thrombosis model we selected the dose of each stimulus to produce 0–15% mortality by each stimulus alone and about 80% mortality by combination of both stimuli.

Test results are tabulated as follows:

TABLE 7

|  | Dose mg/kg | Route | % Protection (% alive mice) |
|---|---|---|---|
| Control |  |  | 0 |
| Ticlopidine | 100 | Oral | 78 |
| S-MPEC | 1 | Oral | 40 |
| S-MPEC | 3 | Oral | 50 |
| S-MPEC | 10 | Oral | 80 |
| S-MPEC | 2.5 | Intrarectal | 60 |
| S-MPEC | 5 | Intrarectal | 90 |
| S-MPEC | 10 | Intrarectal | 90 |
| R-MPEC | 10 | Oral | 25 |

These results suggest that MPEC may be absorbed through the intestine and exert antithrombotic effect. At an oral dose of 10 mg. per kg. of body weight, S-MPEC at 80% protection provides more than triple the 25% protection of R-MPEC. The anti-thrombotic activity expressed here could be crucial to the positive effects of S-MPEC on wound-healing. Part of the problem in that condition is the release of serotonin which does two main things: 1) it causes vaso-constriction (in an attempt to reduce blood loss) which S-MPEC antagonizes and 2) it causes thrombosis (again to reduce blood loss) which S-MPEC antagonizes. Good circulation for wound-healing is essential.

EXAMPLE 6

Effect of S-MPEC on the Inhibition of Rectal Mucosa Blood Flow Caused by Serotonin (5-HT)

Experimental Method

SD strain male rats (b.w. 388–588 g) were fixed in dorsal position under pentobartital-Na (45 mg/kg.I.p.) anesthesia. After the tissue of rectal circumference was exfoliated, the surface of mucosa was made to crop out and fixed on cork board with pin. Cannulae were put on to the right femoral vein and the total carotid artery for 5-HT administration and hemodynamometry, respectively and the probe of laser doppler flowmeter (PeriFlux, Sweden) was attached to the rectal mucosa. S-MPEC suspended in 0.5% Tween 80 was given in rectum after having identified that blood pressure became stable. Ten µg/kg of 5-HT was injected 15 min. after S-MPEC administration. Mucosa blood flow was measured 5 min. and 1 min. after 5-HT injection. Test results are tabulated as follows:

TABLE 8

|  | 5-HT ALONE | 5-HT + S-MPEC | % ANTAGONISM |
|---|---|---|---|
| Reduction in blood pressure (mm. Hg.) | 60 | 60 | 0 |
| Reduction in rectal mucosal blood flow - Flow meter output (volts) | 3.9 | 1.3 | 67 |

These results show that S-MPEC antagonizes the effect of 5-HT in decreasing rectal mucosal blood flow in rats (5 $HT_2$ receptor), but does not antagonize the blood pressure-lowering effects of 5HT on arterial blood pressure ($5HT_1$ receptor).

The following examples illustrate formulations containing pure S-MPEC, optionally admixed with up to about 10%, preferably below about 4%, of R-MPEC, suitable for treating animals, especially humans, in need of a $5HT_2$ receptor blocking effect.

EXAMPLE 7

Topical or Hemorrhoidal Cream

The base of the cream contains:

| | |
|---|---|
| Petrolatum Album | 71.0 gm |
| Liquid petrolatum | 25.0 gm |
| White Beeswax | 3.0 gm |
| Water | 1.0 gm |
| Total | 100.0 gm |

The base is prepared by triturating all the ingredients together until homogenous.

Active Cream:

| | |
|---|---|
| S-MPEC | 1.0 gm |
| Base Cream | 99.0 gm |
| Total | 100.0 gm |

Stability of MPEC in Base Cream (Active Cream)

The stability of the active cream was examined by storing samples of the cream at room temperature (24°–27° C.), 50° C. and 80° C. and under intense fluorescent light for 6 and 12 weeks, and assaying the percentage of the initial S-MPEC remaining after the indicated storage time.

The results are shown in the following table:

TABLE 9

| Condition | Time | Assay |
|---|---|---|
| | 0 | 101.0 |
| Room Temp. | 12 weeks | 100.0 |
| | | 101.1 |
| 50° C. | 6 weeks | 100.3 |
| | | 100.9 |
| | 12 weeks | 99.9 |
| | | 100.4 |
| 80° C. | 6 weeks | 99.9 |
| | | 100.2 |
| | 12 weeks | 100.3 |
| Fluorescent light | 6 weeks | 98.0 |
| | | 99.3 |
| | 12 weeks | 97.8 |
| | | 96.5 |

EXAMPLE 8

Tablet

| Material | Amount |
|---|---|
| S-MPEC | 50.0 g. |
| Magnesium stearate | 1.3 g. |
| Corn starch | 12.4 g. |
| Corn starch pregelatinized | 1.3 g. |
| Lactose | 185.0 g. |

The foregoing materials are blended in a twin-shell blender and then granulated and pressed into tablets weighing 250 mg. each. Each tablet contains 50 milligrams of active ingredient. The tablet may be scored in quarters so that a dose of 12.5 mg. of active ingredient may be conveniently obtained.

EXAMPLE 9

Capsule

| Materials | Amount |
|---|---|
| S-MPEC | 125 g. |
| Lactose | 146.0 g. |
| Magnesium stearate | 4.0 g. |

The foregoing materials are blended in a twin-shell blender and then filled into No. 1 hard gelatin capsules so that each capsule contains 12.5 mg. of active ingredient.

EXAMPLE 10

Intravenous Solution

A sterile solution is prepared by dissolving 10.0 g. of S-MPEC in a minimal amount of 0.5N hydrochloric acid. This solution is adjusted to a pH of 4.3 with 0.1N sodium hydroxide and diluted to 1,000 ml. total volume with saline. The solution is sterilized by passage through a bacteriological filter.

This invention has been disclosed with respect to certain preferred embodiments, and it will be understood that modifications and variations thereof obvious to those skilled in the art are to be included within the spirit and purview of this application and the scope of the appended claims.

I claim:

1. S-|2-(o-aminophenethyl)-1-methylpiperidine-dibenzoyl-L-tartrate salt] (S-APEMP-DBLT).

2. A method of preparing the compound of claim 1 comprising reacting 1 mol of 2-nitrobenzaldehyde with 1 mol of 2-picoline in the presence of acetic anhydride and treating the resulting 2-(o-nitrostyryl)-pyridine with a quarternizing methylating agent to produce the corresponding 2-(o-nitrostyryl)-1-methylpyridinium salt, reducing the pyridinium salt by catalytic hydrogenation to produce the corresponding 2-(o-aminophenethyl)-1-methylpiperidine (RS-APEMP) hydro salt, treating the hydro salt with an alkaline agent to liberate the free base (RS-APEMP) and treating the free base with dibenzoyl-L-tartaric acid to produce S-APEMP-DBLT.

3. A method according to claim 2 followed by liberating the S-APEMP free base from its DBLT salt by treatment with an alkaline agent and reacting the S-APEMP with an equimolar amount of cinnamoyl chloride to produce S-MPEC.

4. A therapeutic composition comprising a pharmaceutical carrier containing as an active ingredient an effective 5 $HT_2$ receptor blocking amount of a compound selected from the group consisting of R-isomer-free S-2'|2-(1-methyl-2-piperidyl)ethyl| cinnamanilide (S-MPEC) and a pharmaceutically acceptable salt thereof, and any mixtures thereof with up to about 10% of any of their corresponding R-isomers (R-MPEC) and salts thereof.

5. A composition according to claim 4, containing in said mixtures about 0.1% to about 4% of the R isomer.

6. A composition according to claim 1 containing S-MPEC or its HCl salt entirely or substantially free of R-MPEC.

7. A composition according to any of claims 4, 5 and 6 in the form of a paste, ointment, cream or gel suitable for topical application wherein said vehicle comprises a gelling, binding or thickening agent to provide the desired viscosity.

8. A composition according to any of claims 4, 5 and 6 in the form of a tablet, capsule, chewing gum, lozenge, powder, aerosol, spray, suppository, enema, syrup, elixir, aqueous or oily suspension, emulsion, or solution, paste, ointment, cream or gel suitable for systemic oral, rectal or parenteral administration as by subcutaneous, intraperitoneal, intramuscular or intravenous injection or transdermal or inhalation therapy.

9. A method of treating an animal in need of a $5HT_2$ receptor blocking effect comprising administering to said animal a therapeutically effective $5HT_2$ receptor blocking amount of a composition as defined in any of claims 4, 5 and 6.

10. A method according to claim 9 for treating or preventing hemorrhoids, varicose veins, or venous or coronary insufficiency, or treating wounds, in such animal.

11. The method of claim 9 wherein said animal is a human.

12. The method of claim 10 wherein said animal is a human.

13. A method of treating an animal in need of a $5HT_2$ receptor blocking effect comprising administering to said animal a therapeutically effective $5HT_2$ receptor blocking amount of a composition as defined in claim 7.

14. The method of claim 13 wherein said animal is a human.

15. A method of treating an animal in need of a $5HT_2$ receptor blocking effect comprising administering to said animal a therapeutically effective $5HT_2$ receptor blocking amount of a composition as defined in claim 8.

16. The method of claim 15 wherein said animal is a human.

17. A method for treating an animal in need of a $5 HT_2$ receptor blocking effect comprising administering to said animal a therapeutically effective $5HT_2$ receptor blocking amount of S-MPEC or a pharmaceutically acceptable salt thereof.

18. A method according to claim 17 for treating or preventing hemorrhoids, varicose veins, or venous or coronary insufficiency, or treating wounds, or providing analgesic or local anesthetic effects in such animal.

19. The method of claims 17 or 18 wherein said animal is a human.

* * * * *

UNITED STATES PATENT AND TRADEMARK OFFICE
CERTIFICATE OF CORRECTION

PATENT NO. : 5,780,487
DATED : July 14, 1998
INVENTOR(S) : Beukema, et al

It is certified that error appears in the above-identified patent and that said Letters Patent is hereby corrected as shown below:

ON THE TITLE PAGE:

Item 54, correct the title to read as follows:

--PHARMACEUTICAL COMPOSITION CONTAINING S-2'-[2-(1-METHYL-2-PIPERIDYL) ETHYL] CINNAMANILIDE--.

Signed and Sealed this

Twenty-third Day of February, 1999

Attest:

Q. TODD DICKINSON

Attesting Officer

Acting Commissioner of Patents and Trademarks